US008211108B2

(12) United States Patent
Matityahu

(10) Patent No.: US 8,211,108 B2
(45) Date of Patent: Jul. 3, 2012

(54) PERCUTANEOUS INTRAMEDULLARY BONE REPAIR DEVICE

(75) Inventor: Amir M. Matityahu, Los Altos, CA (US)

(73) Assignee: Anthem Orthopaedics LLC, Los Altos, CA (US)

( * ) Notice: Subject to any disclaimer, the term of this patent is extended or adjusted under 35 U.S.C. 154(b) by 1046 days.

(21) Appl. No.: 12/013,338

(22) Filed: Jan. 11, 2008

(65) Prior Publication Data

US 2008/0269751 A1 Oct. 30, 2008

Related U.S. Application Data

(60) Provisional application No. 60/884,532, filed on Jan. 11, 2007.

(51) Int. Cl.
*A61B 17/58* (2006.01)
(52) U.S. Cl. .......................... 606/64; 606/62
(58) Field of Classification Search ............. 606/62–68, 606/305–308, 60, 300–304, 309–331, 76, 606/78; 623/22.4–23.46, 19.11–20.13; 411/293
See application file for complete search history.

(56) References Cited

U.S. PATENT DOCUMENTS

| | | | | |
|---|---|---|---|---|
| 4,163,292 A * | 8/1979 | Averett, Jr. | .................. | 623/23.15 |
| 5,181,928 A * | 1/1993 | Bolesky et al. | ............ | 623/22.42 |
| 5,964,768 A * | 10/1999 | Huebner | ....................... | 606/317 |
| 6,270,499 B1 | 8/2001 | Leu et al. | | |
| 6,379,359 B1 * | 4/2002 | Dahners | ........................... | 606/62 |
| 6,613,052 B1 * | 9/2003 | Kinnett | ........................... | 606/62 |
| 6,623,486 B1 * | 9/2003 | Weaver et al. | ................. | 606/281 |
| 6,730,091 B1 * | 5/2004 | Pfefferle et al. | ................. | 606/70 |
| 6,926,719 B2 * | 8/2005 | Sohngen et al. | ................. | 606/64 |
| 7,655,009 B2 * | 2/2010 | Grusin | ............................ | 606/64 |
| 7,896,886 B2 * | 3/2011 | Orbay et al. | .................... | 606/96 |
| 7,909,825 B2 * | 3/2011 | Saravia et al. | .................. | 606/66 |
| 2004/0243138 A1 | 12/2004 | Cole | | |
| 2005/0143739 A1 | 6/2005 | Shinjo et al. | | |
| 2006/0149265 A1 * | 7/2006 | James et al. | .................... | 606/73 |
| 2006/0189987 A1 * | 8/2006 | Orbay et al. | .................... | 606/62 |
| 2006/0235396 A1 * | 10/2006 | Sanders et al. | .................. | 606/69 |
| 2007/0233105 A1 * | 10/2007 | Nelson et al. | ................... | 606/64 |

OTHER PUBLICATIONS

Aug. 7, 2008 International Search Report issued by the ISA/US for corresponding PCT patent application serial No. PCT/SU2008/050810, p. 1.
Aug. 7, 2008 Written Opinion of the International Searching Authority by the ISA/US for corresponding patent application serial No. PCT/SU2008/050810, pp. 1-5.

* cited by examiner

*Primary Examiner* — Eduardo C Robert
*Assistant Examiner* — Jan Christopher Merene
(74) *Attorney, Agent, or Firm* — Dorsey & Whitney LLP

(57) ABSTRACT

An intramedullary bone repair system and device for insertion into a bone extending along a longitudinal axis of the bone and for use with a plurality of screws. The bone repair device includes an elongate shaft and a head pivotally coupled to the proximal end of the shaft. A locking assembly is carried by the proximal end of the shaft and the head for rigidly coupling the shaft and the head together when the shaft and the head have been desirably positioned within the bone. The shaft and the head are provided with a plurality of threaded bores for receiving the plurality of screws to affix the shaft and head within the bone. A method for repair of a bone fracture using the bone repair device is also disclosed.

13 Claims, 12 Drawing Sheets

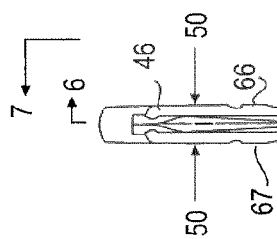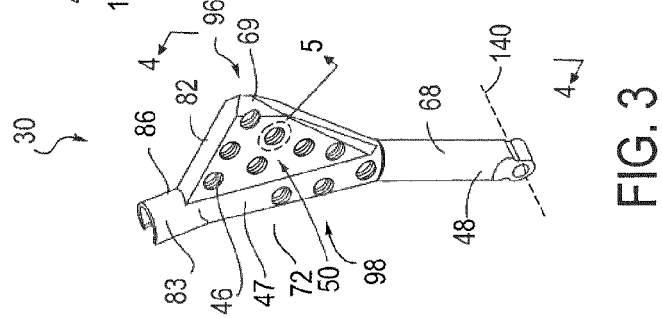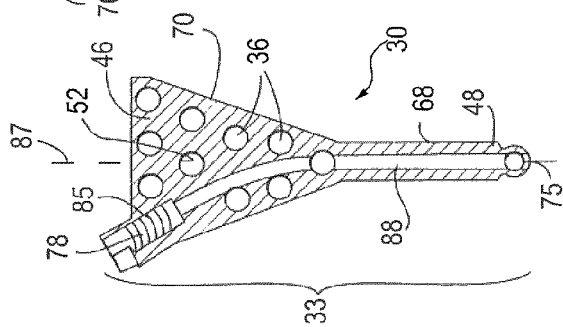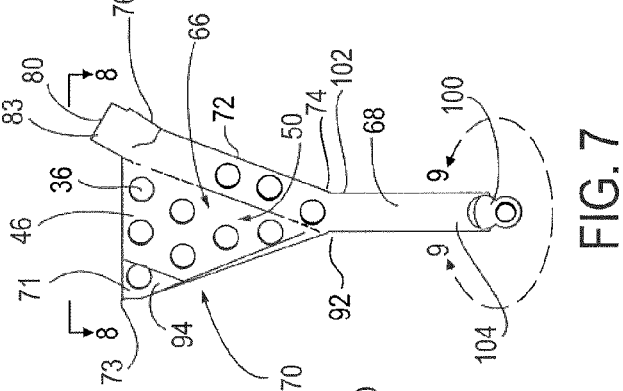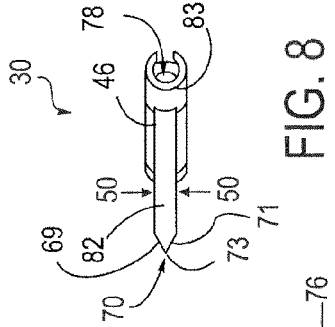

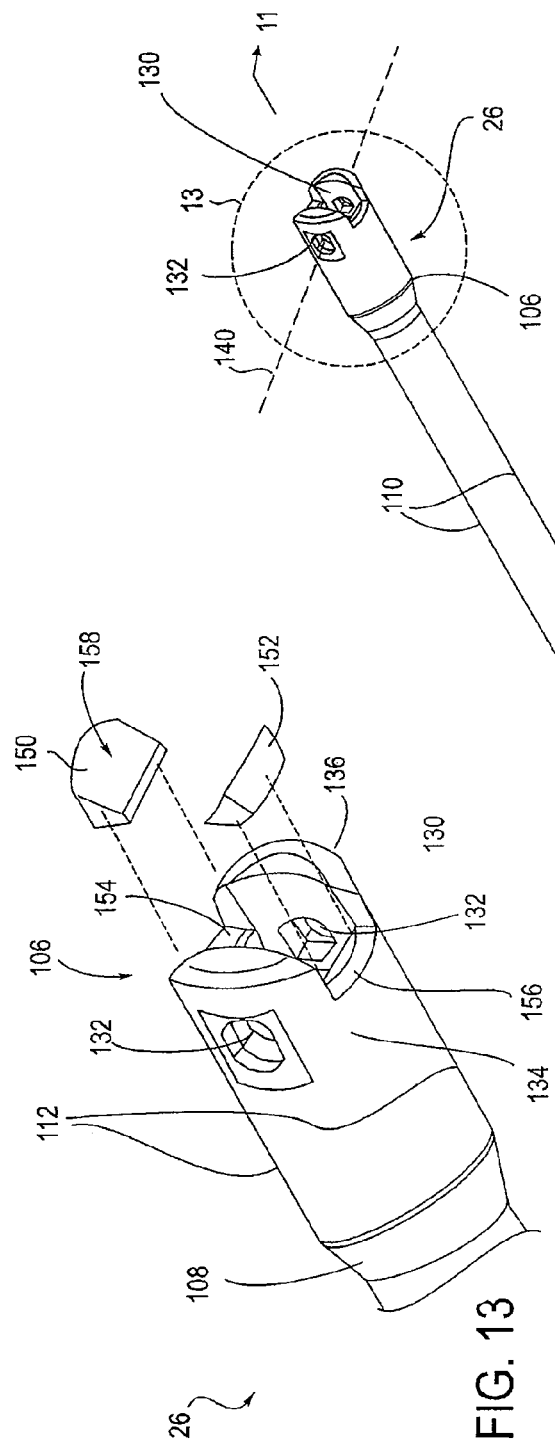
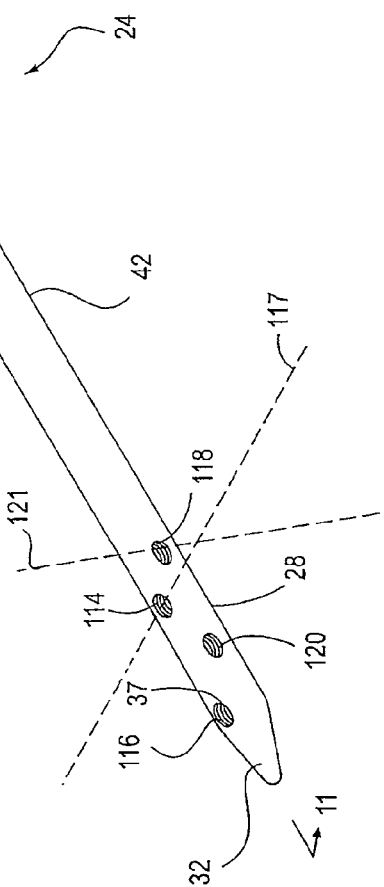
FIG. 10
FIG. 13

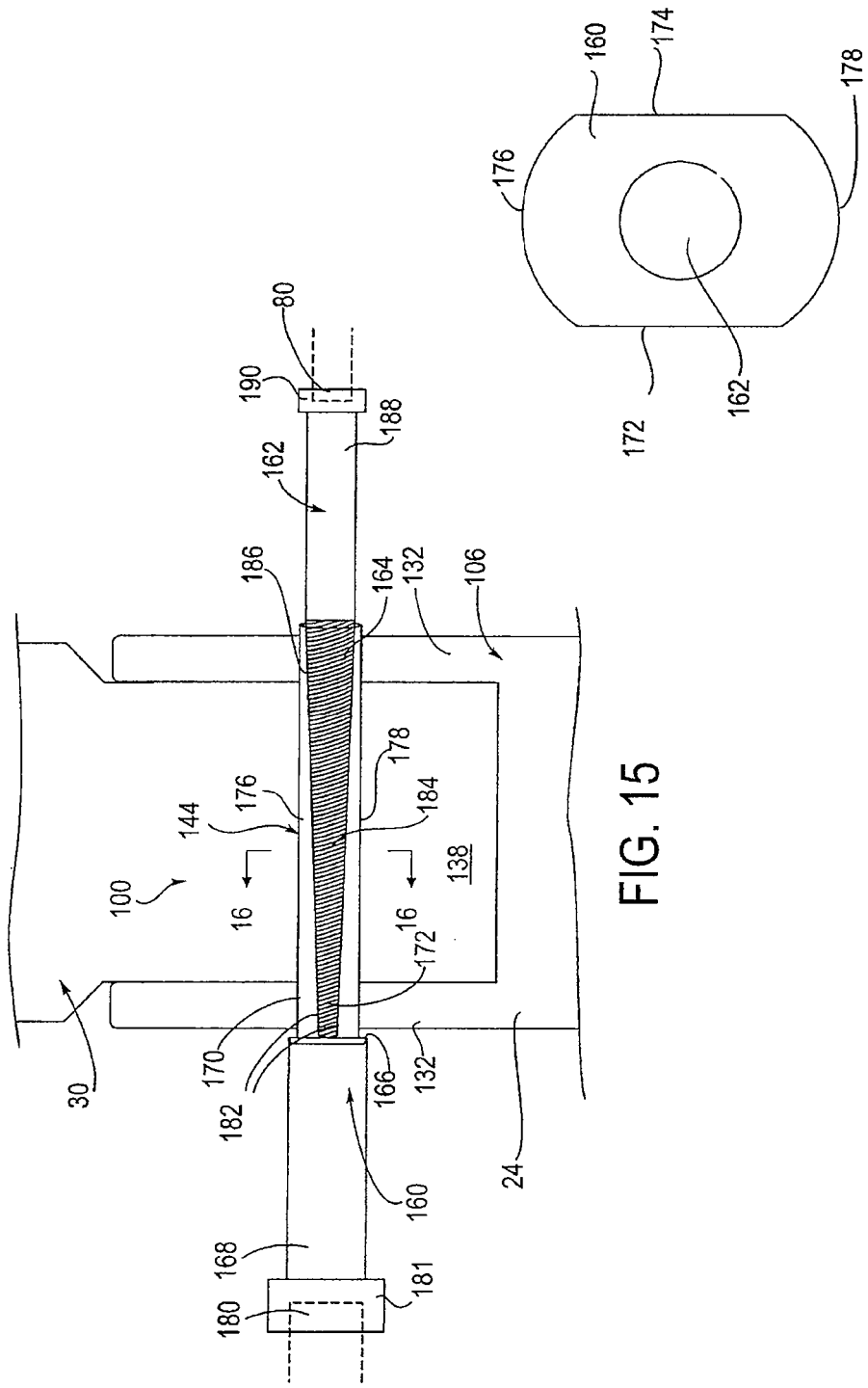

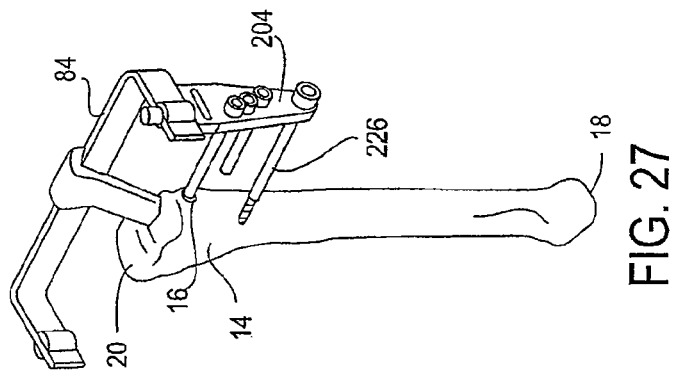
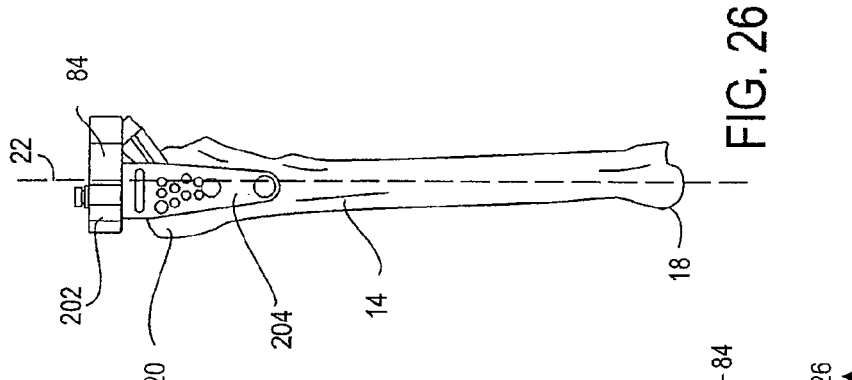
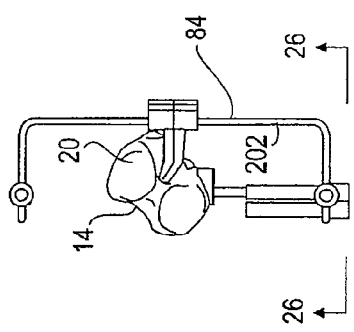
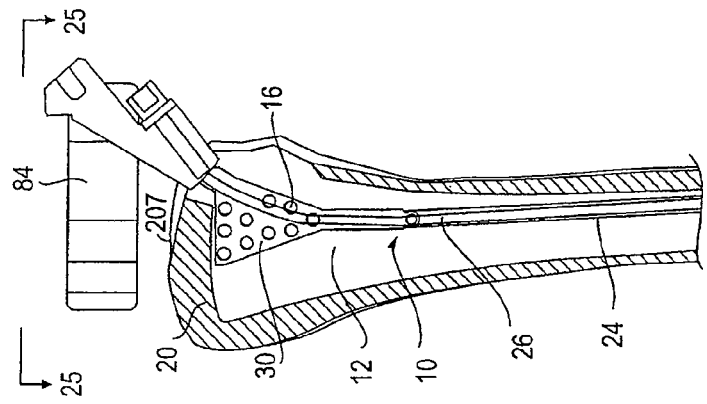

PERCUTANEOUS INTRAMEDULLARY BONE REPAIR DEVICE

SCOPE OF THE INVENTION

The present invention relates to a bone repair assembly, and more particularly a device and method to repair bone fractures.

BACKGROUND

It is known to repair bone fractures using a plate. Typically, a plate is affixed to the side of a fractured bone. It is also known to repair bone fractures using a nail. Currently to fix a fracture of a long bone, such as the femur or tibia, two primary devices exists. To repair a bone fractured at the middle shaft component, or a shaft component within the middle part of the bone, a nail is most commonly used. The nail is inserted into the interior of the bone. The standard for repairing articular fractures, or fractures that go into the joint, or fractures within five centimeters of the joint, on the other hand involves the use and attachment of a plate to the side of the bone.

Unfortunately, both devices suffer drawbacks. Plates attached to the side of a bone, which carry the weight of the patient formerly carried by the now fractured bone, can fail due to moments being placed on the plate by the patient. Specifically, the off-center positioning of the weight bearing plate causes moments to be applied to the screws which attach the plate to the bone. Not only does this place stress upon the fractured area of the bone, but the moment can cause the plate to fatigue. In addition to the foregoing, a doctor must dissect through soft tissue in order to place a plate on the bone. This causes additional trauma to the soft tissue which has already been traumatized by the damage to the bone. If the plate is placed via an open and not percutaneous procedure, the fracture is devitalized and the bone may take longer to heal. In addition to the foregoing, a plate is placed on either the medial or lateral aspect of the bone which may be prominent and painful to the patient.

Nails or rods, which are placed inside the bone to repair a fracture, are typically not inserted along the centerline of the bone. To position the nail in a proper location in the bone, the point of entry of the nail into the bone is typically at the top or top/front of the bone. Thus, for example, when such a device is inserted into the tibia, to insert directly into the centerline of the bone, the position of insertion is at the knee joint. Unfortunately, due to the other structural elements present at the insertion location, current nails are not introduced near the top or end of the bone, but instead near the top along one of the side of the bone. In this location, the nail is not able to extend along the center of the bone over its entire length. Moreover, disadvantages associated with the nail include the inability to fix interarticular fractures, or fractures that extend through the joint and inability to fix fractures within five centimeters of the joint, because of a lack of fixation points. In addition, when a nail is placed into the bone, the rigidity of the nail may cause the doctor to disrupt an interarticular fracture, thus making the fracture of the bone worse.

Current nails may also comprise cumulative tubes which are placed from the traditional starting point of the bone, namely entering from a joint surface. Typically, however, such devices are used for shaft-type tibia fractures, and do not find a use with fractures that are close to the joint, for example within five or six centimeters from the joint.

In addition to the foregoing, a common problem associated with both nails and plates is that they do not include any pivotal components, but are instead a single rigid device. Thus, the devices are extremely limited in where and how they can be used.

Accordingly, what is needed in the art is a percutaneous intramedullary bone repair device that combines the advantages of both the plate and the nail, but is capable of being positioned into the bone along the centerline of the bone so as to effectively reduce the stress of the fractured bone and stress of the device. The device may be attached to the bone to secure the device in place via bone screws or pegs.

SUMMARY OF THE INVENTION

The present invention relates to a bone repair device that includes an elongate shaft and a head pivotally coupled to the shaft. A plurality of screws are provided within a plurality of threaded bores that affix the shaft and head within the bone. A method of using the percutaneous bone repair device includes insertion of the device within the interior of the bone so that it extends along a centerline of the bone and securing the device in position using one or more screws.

BRIEF DESCRIPTION OF THE DRAWINGS

FIG. 3 is a perspective view of the head shown in FIG. 2.

FIG. 4 is an end elevational view of the head taken along line 4-4 of FIG. 3.

FIG. 6 is a cross-sectional view of the head taken along line 6-6 of FIG. 4.

FIG. 7 is a side elevational view of the head taken along line 7-7 of FIG. 4.

FIG. 8 is a top plan view of the head taken along line 8-8 of FIG. 7.

FIG. 9 is a cutaway side elevational view taken along line 9-9 of FIG. 7.

FIG. 10 is a perspective view of the shaft of the bone repair device shown in FIG. 2.

FIG. 13 is a cutaway perspective view of the top of the shaft designated by line 13 of FIG. 10.

FIG. 15 is a cross sectional view of the locking assembly taken along line 15-15 of FIG. 14.

FIG. 16 is a cross sectional view of the locking assembly of FIG. 15 taken along line 16-16 of FIG. 15.

FIG. 24 is a cut-away elevational view of the insertion tool and bone repair device of FIG. 23.

FIG. 25 is a top plan view of the insertion tool and bone repair device taken along line 25-25 of FIG. 24.

FIG. 26 is a side elevational view of the insertion tool and bone taken along line 26-26 of FIG. 25.

FIG. 27 is a perspective view of the bone and insertion tool of FIG. 24.

DESCRIPTION OF THE INVENTION

Figures 1, 2:
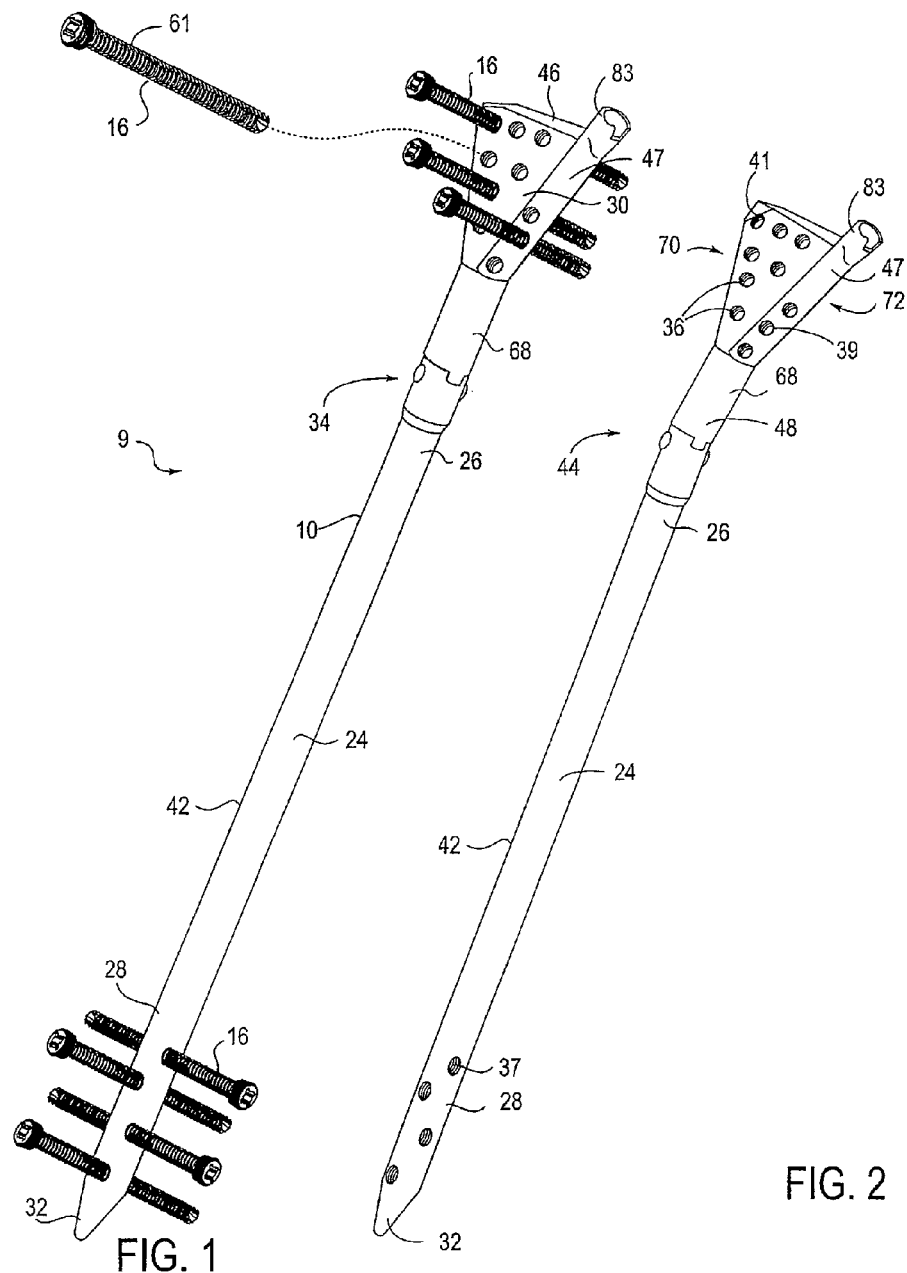
FIG. 1 is a perspective view of a bone repair device of the present invention having screws attached.
FIG. 2 is a perspective view of the bone repair device of FIG. 1 absent the screws and showing the head pivoted.

The figures and description herein describe an intramedullary bone repair system and device. More specifically, a percutaneous intramedullary bone repair system 9 is provided. In this system, the bone repair device 10 is inserted within the interior 12 of the bone 14 and secured in position using one or more fastening devices, such as screws 16. The intramedullary bone repair device 10 is adapted for placement or insertion into a bone 14. The bone 14 has a first end 18 and a second end 20, and a longitudinal axis 22 extending therebetween. The device 10 preferably extends along a longitudinal axis 22 of the bone 14 and is for use with a plurality of screws 16. The device 10 includes an elongate body, shaft or nail 24 having a proximal end 26 and a distal end 28. A head or plate 30 is seated in, and preferably pivotally coupled to the proximal end of the shaft 24. The distal end of the shaft 24 has a tapered end 32 for facilitating insertion of the shaft 24 along the longitudinal axis 22 of the bone 14. A locking assembly 34 is carried by the proximal end of the shaft 24 and the head 30 for rigidly coupling the shaft 24 and the head 30 together when the shaft and the head have been desirably positioned within the bone 14. In order to further secure the bone repair device 10 to the bone 14, the shaft 24 and/or the head 30 are provided with a plurality of threaded bores 36 and/or 37 for receiving a plurality of screws 16 to affix the shaft 24 and/or head 30 within the bone 14.

The bone repair device 10 can be used with any suitable bone of the mammalian body, including, but not limited to, a humerus, radius, ulna, femur, fibula, or tibia. The embodiment described and illustrated herein is for use with a long bone, such as a tibia. The head 30, the shaft 24, the locking assembly 34, and screws 16 described herein are preferably comprised of a rigid material, such as titanium or stainless steel. However, it is contemplated that plastics, composites, resorbable materials, metals and/or other materials or combinations thereof which are suitable for insertion within a mammalian body may be used for one or more of the components of the bone repair device 10 described. Likewise, in a preferred embodiment, the shaft 24 and head 30 are not flexible, but flexible components may be used based upon user preferences.

Device 10 includes a proximal portion or head 30 and a distal portion or shaft 24 that is preferably pivotably coupled to the head 30. Head 30 can be of any suitable type and in one embodiment, as illustrated in FIGS. 1-9, is formed from an integral body 33 having a proximal portion 46 that is plate-like in shape and a distal portion 37 that is cylindrical in shape. The proximal portion or plate 36 is preferably triangular in plan, as shown in FIG. 7, and tapers inwardly as it extends distally to the distal portion 48 or neck 68. The plate includes first and second planar surfaces 66 and 67 extending between the back or posterior edge 70 of the head and the front or anterior edge 72 of the head. In this regard, the proximal portion of the head 30 may be in the shape of a plate. The plate-like surfaces of the head 30 comprise an engagement surface 98 or member for receipt of the screw(s). The engagement surface 98 of the head 30, comprises a plurality of threaded bores 36 adapted for receiving a plurality of screws 16. The posterior edge 70 of the plate is formed by first and second surfaces 69 and 71 which taper inwardly from respective side surfaces 66 and 67 to a leading edge 73. This wedge-shape section 96 assists in the forced movement of the head 30 of the bone repair device 10 into the bone 14 as it is pivoted toward the centerline 38 of the bone 14. The front 72 of the plate includes a cylindrical-shaped rib 47 which extends along the length of the front portion 72 The plate 46 includes a proximal or top end preferably formed by a top planar surface 51. The rib 47 has a portion in the form of cylindrical collar 83 that extends above top surface 82. The front portion 72 also includes an insertion tool attachment bore 78. The insertion tool attachment bore 78 is positioned on a sloped surface 80 extending between the front portion 72 and the top surface 82 of the head 30. The slope of surface 80 is suitable for attachment of an insertion tool 84 so as to permit the use of the insertion tool 84 to both insert the bone repair device 10 into the bone 14 and to pivot the head 30 toward the centerline 38 of the bone 14. In a preferred embodiment, the anterior portion 72 includes the cylindrical collar 83 as an insertion tool receptor portion 86 which extends above the top surface 82 of the head 30 (See FIGS. 6 & 7). The insertion tool receptor portion 86 may include bore 78 for engaging an insertion tool 84. Neck 68 extends distally of the head and is preferably centered a longitudinal axis 87 extending along the center of head 30.

Figure 5:
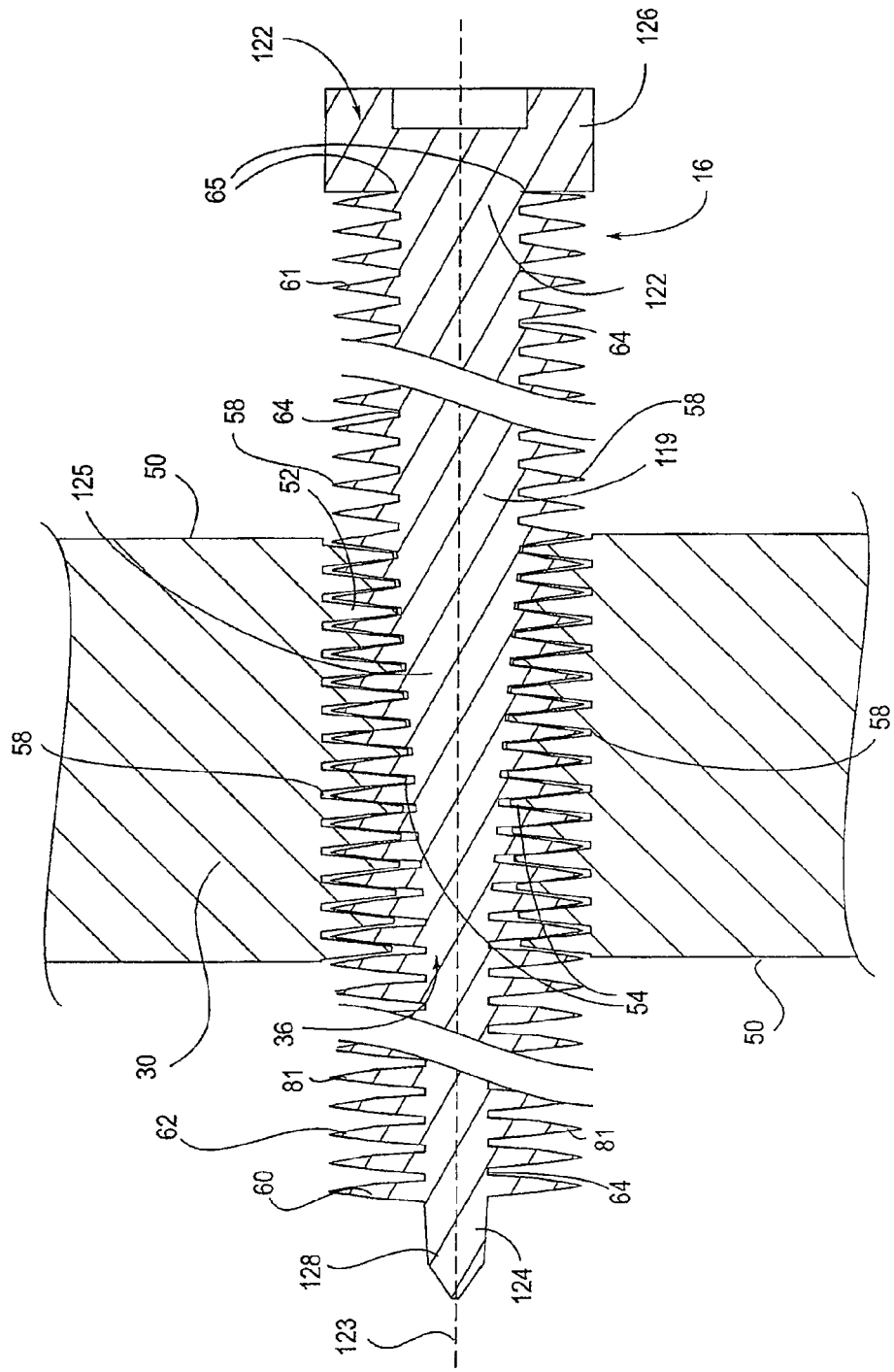
FIG. 5 is an enlarged cross-sectional view of the head, taken along line 5-5 of FIG. 3, with a portion of a bone screw disposed in the head.
Figure 11:
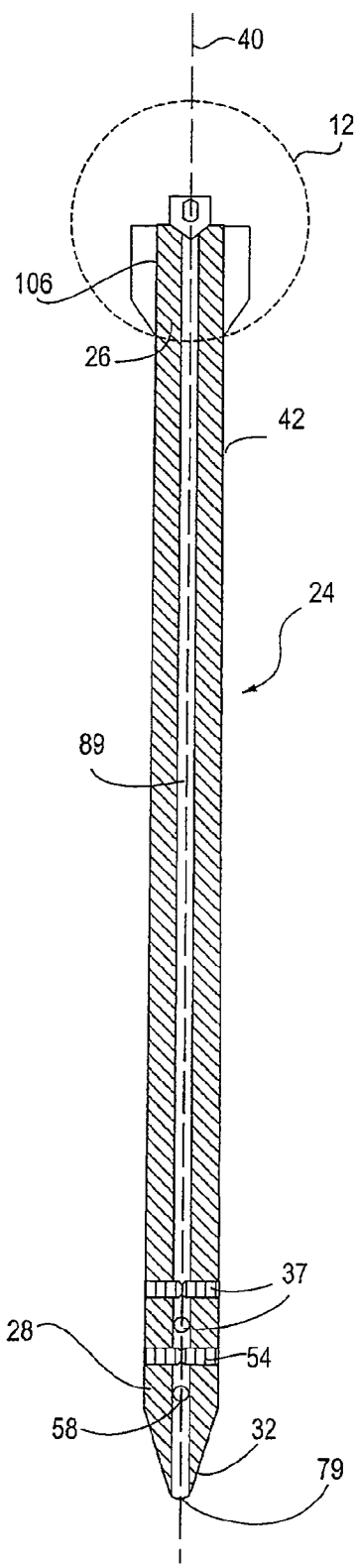
FIG. 11 is a cross sectional view of the shaft taken along line 11-11 of FIG. 10.
Figure 12:
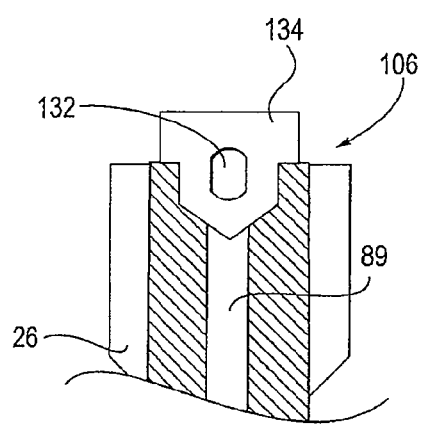
FIG. 12 is a cross-sectional view of the top of the shaft designated by line 11 of FIG. 11.

The head 30 is provided with a plurality of threaded bores 36 or apertures extending between first and second planar surfaces 66 and 67. The bores or apertures 36 may be arranged in any suitable configuration or array. In a preferred embodiment, the head 30 has first and second planar surfaces 66 and 67 through which a plurality of threaded bores 36 extend in a non-linear array. However, a linear array would not depart from the overall scope of the present invention. The plurality of threaded bores 36 in the head 30 may extend parallel to each other. Each bore or threaded bore 36, as illustrated in FIG. 5 with respect to one of the bores 36, extends inwardly from an external surface 50 of the head 30 and has an internal thread 52, extending inwardly from the surface 50. The internal thread 52 of each bore 36 preferably has an inner diameter 54, located at the outer ridge of the thread, that tapers inwardly from each of the external surfaces 50 and has a minimum inner diameter 54 at a location inside of the bore 52 and preferably at the center of the bore. Each thread 52 has an outer diameter 58, located at the trough of the thread, that is preferably constant along the entire length of the bore 35. In an alternative embodiment, bore 36 may be provided with threads of constant inner and outer diameters. The cylindrical rib 47 of the head 30 may also include one or more bores 36, or openings, therethrough. At least one threaded bore 41 may also be in at least partial contact with the wedge-shape portion of the head 30.

Shaft or nail 32 can be of any suitable shape and is preferably cylindrical in conformation. Shaft 24, as illustrated in FIGS. 10-13, comprises an elongate shaft or body having an external or outer surface 42 extending circumferentially around the shaft and a length approximating the transverse dimension of the bone 14 into which the bone repair device 10 is inserted and used. The shaft has a proximal portion 26 and a distal portion 28. The distal end or portion 28 of the shaft 24 has a tapered portion 32 that is preferably rounded at its end. The tapered distal end 32 of the shaft facilitates insertion of the shaft 24 along the center of the bone 14. The proximal end or portion 26 of the shaft 24 may be attached to the head 30.

In a preferred embodiment, as shown in FIGS. 10 & 13, the shaft 24 is provided with a narrow distal portion 28 and an enlarged proximal portion 26 separated by a tapered portion 108. The narrow distal portion or end 28 has a first diameter and may be of any suitable length. The enlarged proximal portion 26 has a second diameter greater than the diameter of the distal portion 28 and may be of any suitable length. The tapered portion 108 is longitudinally positioned along a length of the shaft 24 between the narrow distal portion 28 and the enlarged proximal portion 26. The tapered portion 108 tapers outwardly from the narrow distal portion 28 to the enlarged proximal portion 26, and may be of any suitable length.

The shaft 32, as illustrated in FIGS. 2 and 10, is provided with a plurality of threaded bores 37 extending inwardly from circumferential surface 42. The bores 37 receive threaded screws. The bores 37 are arranged at or near the distal portion 28 of the shaft 24. A first bore 114 and a second bore 116 are spaced apart longitudinally along the shaft and arranged in a first plane 117. A third bore 118 and a fourth bore 120 are spaced apart longitudinally along the shaft and arranged in a second plane 121 perpendicular to the first plane. Thus, the distal end 28 of the shaft 24 is or may be secured to the bone 14 along two axes, thereby providing a stable attachment of the bone repair device 10 to the bone 14. In one preferred embodiment, the bores 37 in the shaft 24 are identical to the threaded bores 36 in the head 30. While a plurality of threaded bores 37 are specifically disclosed, a single bore, an unthreaded bore, and alternative means of attachment would be acceptable for the purposes provided. Likewise, while a perpendicular arrangement of bores 114, 116, 118, 120 is specifically described, alternative angles, for example ranging from zero to 90 degrees, would be acceptable for the purposes provided.

Device 31 includes a pivot assembly 44 for pivotably coupling the head 30 to the shaft at the proximal end 26 of the shaft 24. The neck 68 on head 30 is provided with an integral pivot member 100 forming a portion of the pivot assembly 44 and locking assembly 34. More specifically, the proximal end 102 of the neck 68 is attached to the engagement member 98 and the distal end 104 of the neck 68 has a first pivot member 100 for mating with and engaging a second pivot member 106 connected to the proximal end 26 of the shaft 24. In the preferred embodiment, the second pivot member 106 includes a recessed portion 130 on the proximal end 26 of the shaft 24 for receiving and engaging the first pivot member 100.

The shaft 24 in the embodiment shown in FIGS. 10 & 13, is connected to the second pivot member 106 of the locking assembly 34 through outwardly tapered portion 108. As a result, the diameter 110 of the shaft 24 is narrower than the diameter 112 of the locking assembly 34. However, the diameter of the shaft 24 may be of equal or greater size than the locking assembly 34 without departing from the overall scope of the bone repair device.

The first pivot member 100 of the locking assembly 34 has an outer cylindrical surface 142 having an inner opening 138. Openings or apertures 132 are also provided in the first sidewall 134 and second sidewall 136 of the second pivot member 106. When the outer cylindrical surface 142 of the first pivot member 100 is received within the recess 130 of the second pivot member, openings or apertures 132 in the first sidewall 134 and second sidewall 136 of the second pivot member 106 are aligned with the bore or opening 138 in the first pivot member 100. The sidewalls 134, 136 of the second pivot member 106 are also received within a first recessed portion 137 and a second recessed portion 139 on the first pivot member 100. The first pivot member 100 pivots over the second pivot member 106 about the axis 140 defined by the openings or apertures in the pivot members (see FIGS. 9, 12, & 14).

A clip 220 preferably attaches to the neck 68 and the shaft 24 of the bone repair device 10 prior to insertion of the device 10 into the bone 14. The clip 220 is sufficiently rigid to retain the head 30 and the shaft 24 in the same orientation, centering the head 30 over the shaft 24, thereby preventing action by the pivot assembly 44.

A locking assembly 34 is included in device 10 for locking head 30 in a desired position relative to nail 24 once the head and nail have been pivoted relative to each other.

The pivotal connection or assembly 44 makes up at least a portion of a locking assembly 34 that is carried by the proximal end 26 of the shaft and the head 30 for rigidly coupling the shaft 24 and the head 30 together. Preferably, the locking assembly 34 rigidly and pivotally couples the shaft 24 and the head 30 together after placement in the desired or proper position in the bone 14.

Figure 14:
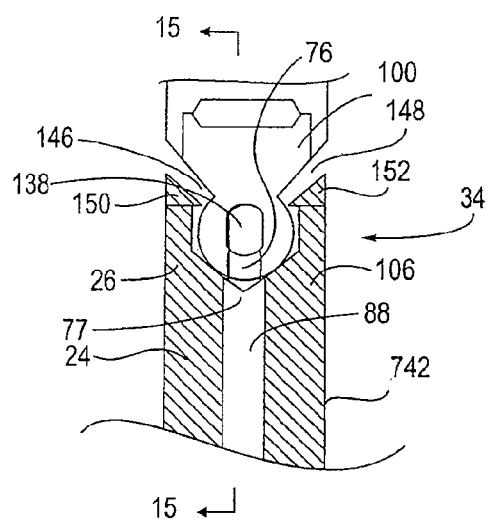
FIG. 14 is a cutaway cross-sectional view of the locking assembly.

The first pivot member 100 has a first groove 146 and a second groove 148 positioned between the outer cylindrical surface 142 and the neck 68 on a first side 149 and a second side 151. The first groove 146 and/or second groove 148 are adapted to receive a stopper or locking wedge 150 positioned on the shaft 24, as illustrated in FIG. 14.

The second pivot member 106, as shown in FIG. 13, includes one or more stoppers 150, 152 or locking wedges positioned near the proximal end 26 of the shaft 24. A first stopper 150 and a second stopper 152 are positioned laterally on a first side 154 and second side 156 of the recessed portion 130 of the second pivot member 106. In a preferred embodiment, the first and second stoppers 150 are removable. Specifically, following engagement of the pivot members 100, 106, the stoppers 150, 152 may be attached to the second pivot member 106. The stoppers 150, 152 extend inwardly toward the attached pivot member 100, resulting in a narrowed recess 130 at that position. The narrowed recess 130 retains the first pivot member 100 in position. The first and second stoppers 150, 152 each also include an inclined surface 158. First and second stoppers 150, 152 are aligned with the first and second grooves 146, 148 on the first pivot member 100. Upon the pivotal movement of the head 30, the first pivot member 100 contacts an inclined surface 158 of the stopper 150 or 152 when pivoted to the greatest extent. Thus, the stoppers 150, 152 limit the pivotal movement of the head 30 when engaged with the shaft 24, and prevent the head 30 from being removed from the shaft 24 by narrowing the size of the recess at the location of the first groove 146 and the second groove 148 on the first pivot member 100.

The inner opening 138 of the first pivot member 100 of the locking assembly 34 is adapted to receive a locking pin or member 144 such as a nut 160 or sleeve, as illustrated in FIG. 9. Openings 132 of the second pivot member 106 are aligned and extend through first and second sidewalls 134, 136 of the second pivot member 106 on opposing sides of the recessed portion 130 of the shaft 24. Openings 132 are also adapted to receive a locking pin or member 144, such as nut 160. In a preferred embodiment, openings 132 and 138 are equivalent These openings 132 and 138 are aligned to receive a corresponding shaped sleeve or nut 160. Once the nut 160 is inserted into the correspondingly shaped openings, the first and second pivot member are unable to pivot about the axis 140. The head 30 is locked in position, centered with the shaft 24 and the centerline of the bone.

The receptor sleeve or nut 160 of the locking assembly 34 is capable of receiving of a screw 162 having an external thread 164. FIG. 15 illustrates the nut 160 or sleeve and corresponding screw 162. The nut 160 preferably has a shape that corresponds to the shape and dimension of the openings 132, 138 in the first pivot member 100 and second pivot member 106. More specifically, the sleeve or nut 160 has a shoulder 166 wider than the opening 132, 138 that seats the nut 160 within the opening in the pivot members of the locking device. Therefore, the nut 160 may be inserted into the aligned openings 132, 138, and upon contact of the shoulder 166 with the pivot member 106 insertion stops. This insertion of the nut 160 prevents pivoting of the pivot members 100 and 106. The nut 160 also may also have an extended unthreaded portion 168 and a locking portion 170. The locking portion 170 of the nut 160, and the openings 132, 138 of the first and second pivot member 100, 106, as illustrated in FIGS. 14 & 16, comprise a first planar wall 172 and a second planar wall 174 connected by a first semicircular wall 176 and a second semicircular wall 178. Thus, the nut 160 has, on at least a portion of its length, a shape which corresponds with the shape of the opening 132, 138 or bore in the pivot member(s). The sleeve or nut 160 also has a tool receptor portion 180 integral with a head 181, such as a socket receptor. Alternative tool receptors would be acceptable for the purposes provided. The inner diameter 182 of the sleeve or nut 160 is open to receive a screw 162 and contains an inner thread 184 along at least a portion thereof for receiving a screw 162 with an external thread 164. Preferably, the screw 162 has a threaded portion 186 and an extended, unthreaded portion 188. The screw also has a head 190 with a comparable tool receptor portion 180. The threaded portion 186 of the screw 162, and the corresponding threaded inner diameter 182, 184 of the nut 160, are tapered, although such an arrangement is not necessary for purposes of the present embodiment. The screw 162 may be rotationally inserted into the nut 160 or sleeve to secure the nut 160 in position in the locking assembly 34. The nut 160 and corresponding screw 162 have an extended unthreaded portion 168, 188. The extended portion 168 and/or 188, however, may or may not have an external thread. Likewise, the inner diameter of the extended portion 168 of the nut 160 may optionally have an inner thread. The extended portion 168, 188 separates the head 180 of the nut 160 and the head 190 of the screw from the operational portions 170, 186 of the respective devices. In an alternative embodiment, the extended portion may not be present.

Device 10 is provided with a bore or passageway 88 extending longitudinally therethrough. In this regard, head 30 has a bore or passageway 88 extending from an opening 78 in cylindrical collar 83 through plate 30 and neck 68 to an opening 75 in and through the first pivot member 100 perpendicular to opening or aperture 138. Opening or passageway 88 has a diameter sufficient to receive a guide wire 90 or 218 to be used in the insertion of the device. Bore or passageway 89 extends through the shaft or nail 24. More specifically, an opening 77 or aperture is provided in the proximal end of the shaft. The passageway 89 extends through the opening 77, which is positioned in second pivot member 106 perpendicular to the openings 132 in the second pivot member. The passageway 89 also extends longitudinally from the opening through the shaft 24 to an opening 79 at the distal end of the shaft. The passageway 89 of the shaft has a diameter sufficient to receive a guide wire 90 or 218 to be used in the insertion of the device 10. In a preferred embodiment, the passageway 88 in the head 30 is aligned with the passageway 89 in the shaft.

Any suitable type of bone screw or peg, solid or cannulated, may be used with bone repair device 10. While a plurality of screws 16 are specifically illustrated herein, a single screw or alternative fastening mechanisms and/or devices may be acceptable for the purposes provided. One preferred embodiment of the screw 16 is illustrated in FIGS. 1 and 5. The screw 16 is an externally-threaded screw 16, having a tapered threaded portion 56 that can be seated in the internal bore 36 or 37 of the head 30 or shaft 24 when affixing the head 30 or shaft 24 to the bone 14. The screw includes an elongate shaft 119 extending along a longitudinal axis 123 and having a proximal portion or shaft segment 122, a distal portion or shaft segment 124 and a central portion or shaft segment 125 between the proximal segment 122 and the distal segment 124. The distal end 124 of the screw is provided with a pointed distal tip 128 that is self tapping and optionally self drilling. The proximal end 122 of the screw 16 has a tool engaging head 126 for receipt of a tool, such as a socket, although other tools and receptors would be acceptable for the purposes provided. In one embodiment, the head may be tapered as it extends distally so as to be conically shaped and may be externally threaded. A tool is engaged with the head 126 and used to rotationally insert the screw 16 into the bone 14 and/or the bone repair device 10.

The shaft 119 of each screw 16 is provided with external threads 60 formed by a raised helical ridge 61 that has an outer diameter 62 which defines the outer diameter of shaft 119. The external thread 60, as illustrated in FIGS. 1 and 5, preferably has a constant outer diameter 58 along the entire length of the shaft 119. The shaft 119 of the screw has an inner diameter 64, located at the trough between each ridge 61, that is constant at the proximal segment 122 and distal segment 124 of the screw. The inner diameter 64 of the shaft 119 at the central segment 125 of the screw tapers inwardly from a first diameter 65 at end of the proximal segment 122 of the screw to a second, smaller diameter 81 at the beginning of the distal segment 124 of the screw. As a result, the depth of the external thread 60 increases in the distal direction along the central segment 125 of the shaft 119, but the outer diameter 62 of shaft 119 remains constant. The inner diameter 64 of the distal segment 124 is small than the inner diameter 64 of the proximal segment 122.

In a further preferred embodiment of the screw 16, externally threaded shaft 119 of screw 16 may be provided with an external thread 60 having an outer diameter 62 approximating the outer diameter 58 of the internal thread 52 of the bore 36, and an inner diameter 64 approximating the minimum diameter 54 of the internal thread 52 of bore 36. In this embodiment, the inner and outer diameters are both constant.

It is preferable that such pullout force be high so as to inhibit undesirably dislodging of a bone screw from a bone. In this regard, helical ridge 61 of the screw 16 preferably has a constant outer diameter 63 over the length of shaft 119 so as to engage the entire side surfaces of the internal threads of the bore 36 over the entire length of the bore and thus enhance the engagement force and the pullout force between the screw 16 and the device 10. The outer diameter of the ridge 61 can range from one to ten millimeters.

The screw 16 can be seated in the internal bore 36 of the head 30 and/or internal bore 37 of elongate body 24 when affixing the device 10 to the bone 14. A sleeve (not shown)

may also be provided, which is carried in a bore 36 of the head 30 or bore 37 of shaft 24. The bore 36 or 37 may or may not have an internal thread in this embodiment. The sleeve preferably comprises an inner thread. The sleeve may receive an attachment bolt or screw 16 having an intermediate taper 56.

In one embodiment, the internal thread of the bore 36 may have an outer diameter that is constant and approximates the outer diameter of the externally threaded screw. Additionally, while a "screw" is specifically described herein, alternative fastening devices would be acceptable for the purposes provided, including, but not limited to, an attachment bolt having an intermediate taper for seating in a bore.

Thus, the present invention combines a nail and plate into a single device. Contrary to current devices, the head 30 pivots in relation to the shaft 24 which permits the top of the device 10 to be moved toward the center the bone 14 after the shaft 24 has been placed. Moreover, the device can be locked in this position by threading screws 16 into the bone 14 and device 10. The engagement of the external threads 60 of the screw, having a constant outer diameters 62 of shaft 119, with the internal threads of the bore 52 increase the force necessary to pull screw 16 out from the device 10 and thus the bone in which the screw is being used to secure the device 10.

Figure 17:
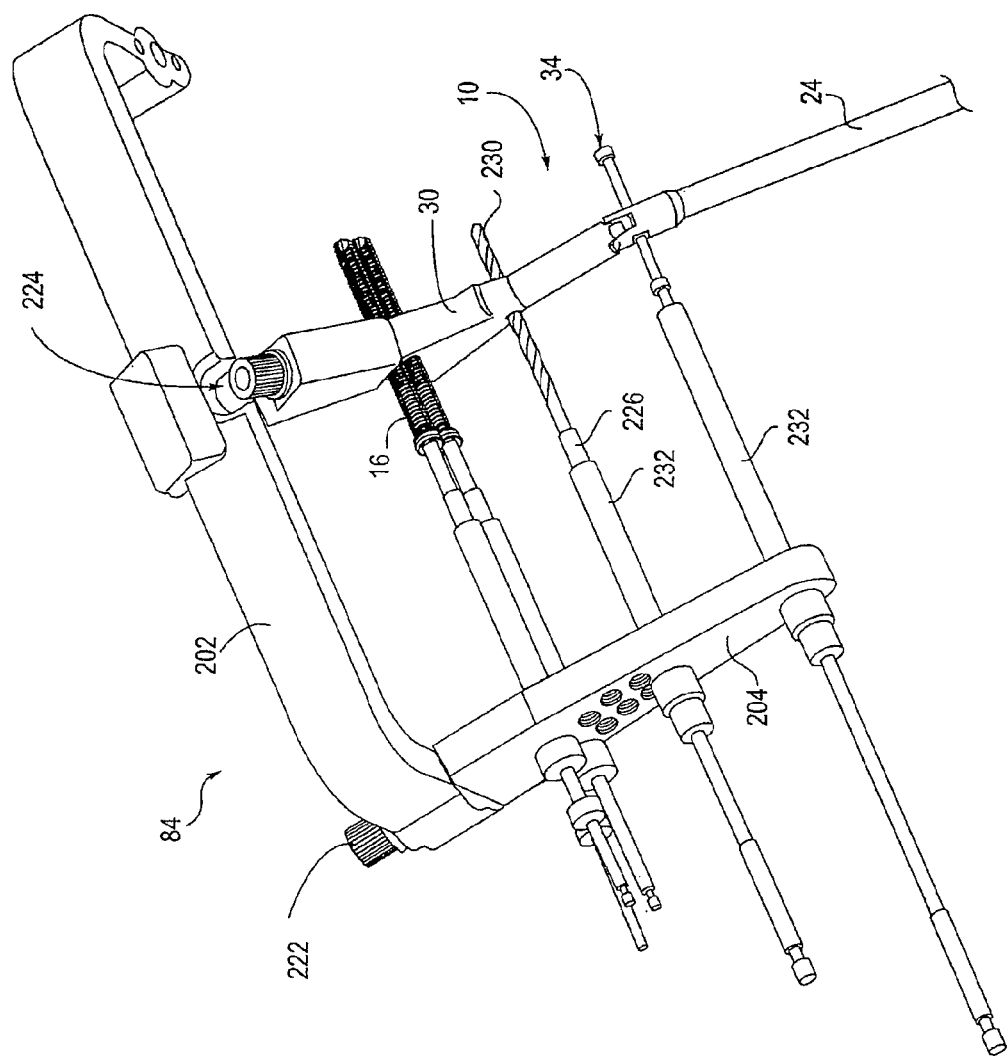
FIG. 17 is a perspective view of an insertion tool attached to the bone repair device 10 of FIG. 1.
Figure 28:
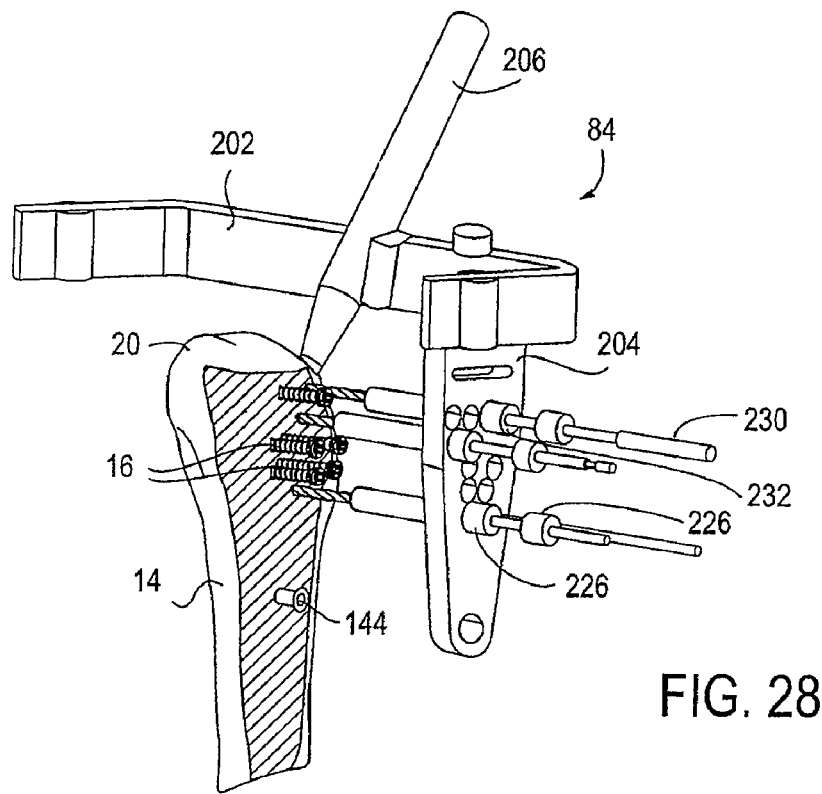
FIG. 28 is a cut-away perspective view of the insertion tool of FIG. 17 and bone.
Figure 29:
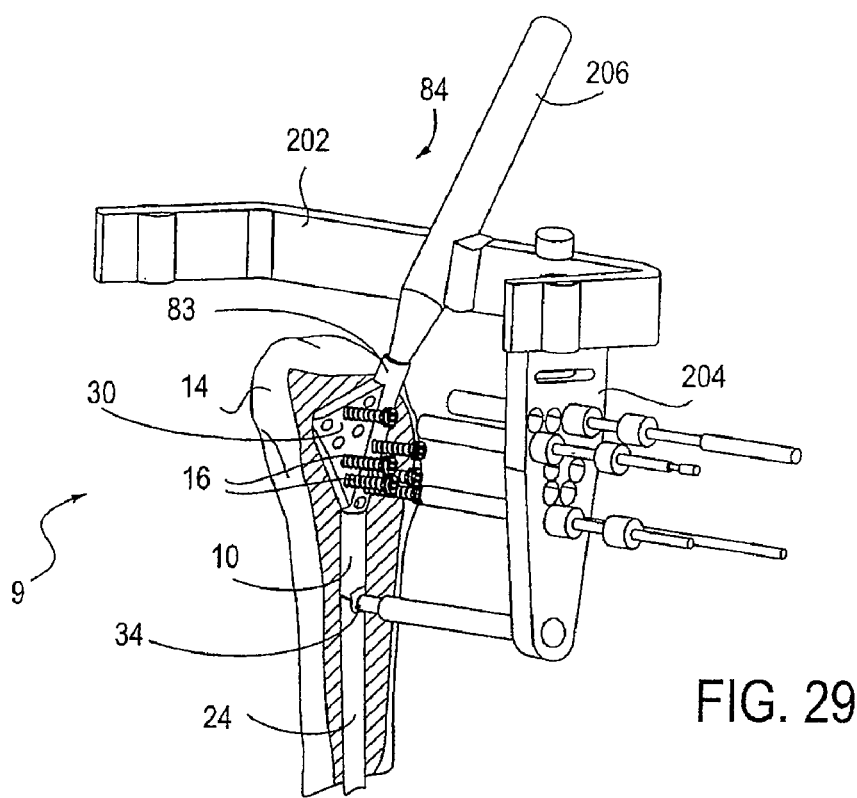
FIG. 29 is a further cut-away perspective view of the insertion tool of FIG. 28.

One preferred method and operation of the invention is illustrated in reference to FIGS. 17-29. The method generally comprises the steps of using an insertion tool or jig 84 for insertion of the bone repair device 10 into the bone 14. FIG. 17 illustrates an example of an insertion tool 84, such as jig 84, as may be used with the present invention, but for ease of reference does not include anvil 206 as is illustrated in, for example, FIGS. 28 & 29.

Figure 23:
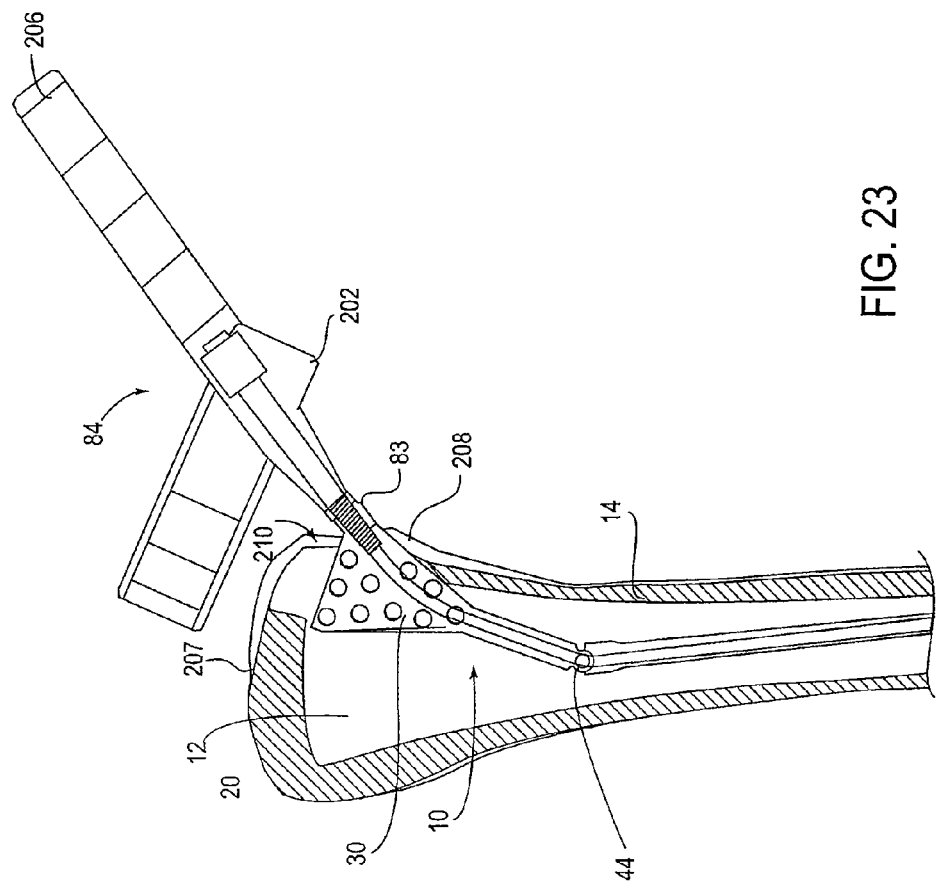
FIG. 23 is a perspective view showing the attachment of the insertion tool to the bone repair device shown in FIG. 22.

In a preferred embodiment, as illustrated in FIG. 23, insertion jig 84 includes an anvil 206, a yolk 202 and an arm 204, and is connected to the bone repair device 10 at the insertion tool attachment bore 78 or cylindrical collar 83 on the head 30 to facilitate further placement of the device 10 into the bone 14. Specifically, the yolk 202 is attached to the cylindrical collar 83 which may be threaded, having an internal thread 85 to receive an external thread (not shown) on the yolk 202 of the insertion tool 84, so that the insertion tool may be secured to the bone repair device 10 for insertion into the bone. The insertion jig 84 also has a targeting device attached to it. The jig 84 includes an arm 204 or plate that extends parallel to the planar sides of the head 30 of the bone repair device 10. The insertion jig 84 attaches, by means of a bolt 222, to the plate 204. Specifically, the arm 204 is attached to the yolk 202. An anvil 206 is also received by a receptor 224 on the yolk 202. The arm 204 of the jig 84 receives a drilling sleeve 226 to assist in drilling of the bone 14 and insertion of screws 16 into the bone 14 and corresponding openings in the head 30. The arm 204 has a plurality of openings 228 or holes positioned to correspond with the bores 36 or openings in the head 30 of the bone repair device 10. In other words, the arm 204 has a plurality of pilot holes 228 and positioning means that permit the accurate placement and insertion of the screws 16. For example, the openings 228 or pilot holes permit a sleeve and trocar assembly (not shown) to be carried by the targeting device.

At the outset of the operation, an opening or entry portal 210 is created in or near the end 20 of the bone 14. Bone 14 is surrounded by tissue in the mammalian body, and has a first end 18 and a second end 20, and a longitudinal axis 22 extending therebetween. A long bone, such as the tibia, has a central or intraventral canal 12 capable of receiving a nail or device 10. The bone 14 also has a top surface 207 and a side surface 208 adjacent a joint. For example, in a tibia, the top surface of the bone in contact with the knee-joint (not shown).

Figure 19:
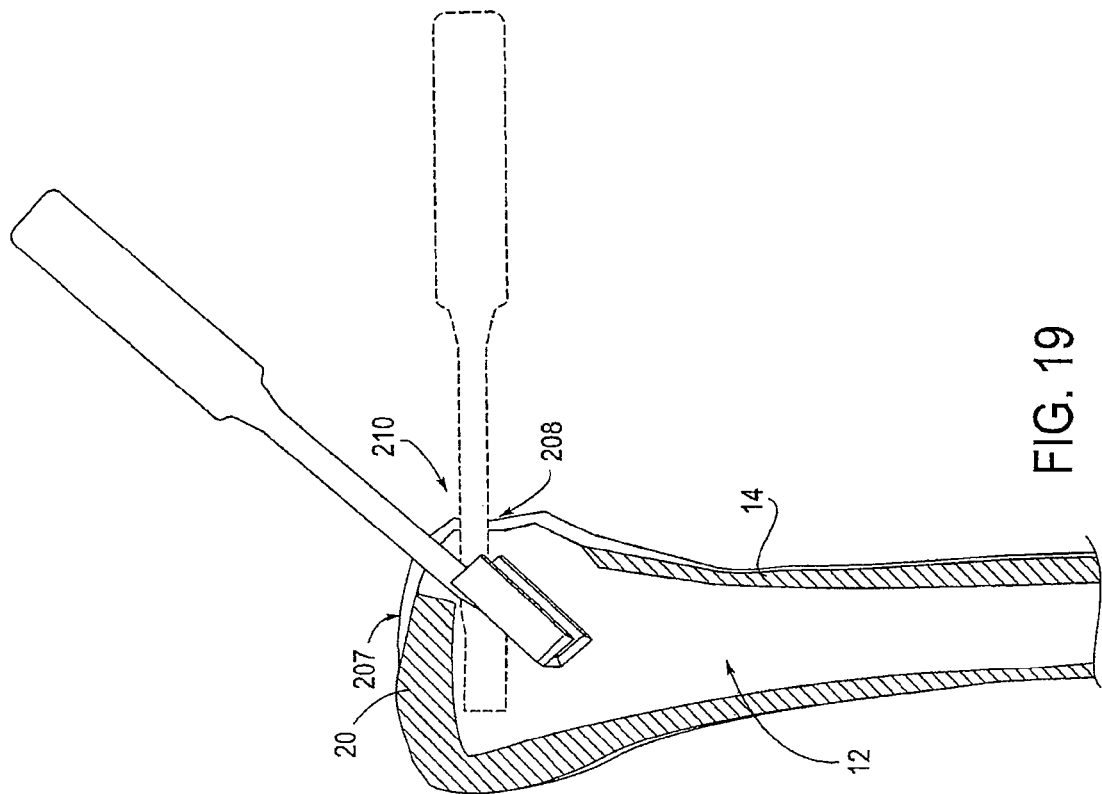
FIG. 19 is a cutaway elevational view showing the positioning and use of a box osteotome in a method of insertion of the bone repair device of FIG. 1.
Figure 18:
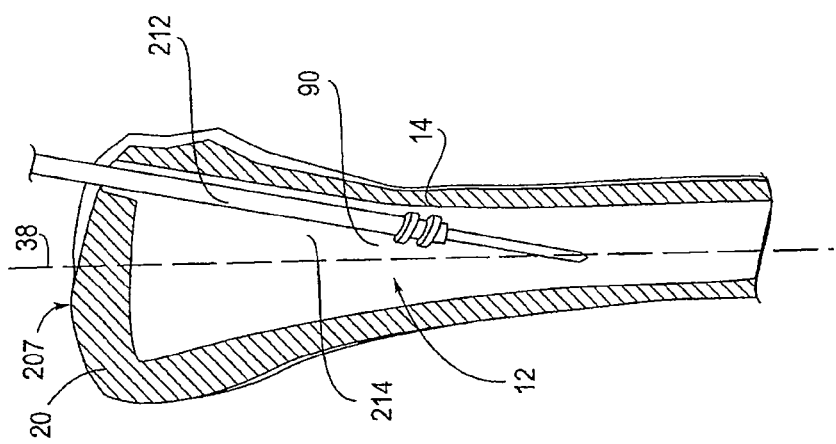
FIG. 18 is a cutaway elevational view showing the use of a reamer to create an entering opening in the bone for insertion of the bone repair device of FIG. 1.

In one preferred embodiment, entry portal 210 in the bone 14 is created in the top surface 207 of the bone, as illustrated in FIG. 18, and then expanded to a side surface 208 adjacent the joint, as illustrated in FIG. 19. Insertion of device 10 may, alternatively, include insertion of the bone repair device 10 directly through a joint.

More specifically, a scalpel makes an initial incision in the tissue surrounding the bone 14. Then a guide wire 90 is inserted into the center of the bone 14. Specifically, a sharp, short guide wire 90 is inserted into an entry opening in the bone 14. A reamer 212 is used to create and entering hole or opening 210 for the later insertion of the bone repair device 10. Specifically, a canal is reamed over the guide wire 90, which increases the size of the intraventral canal 12. The entry opening 210 is created using the end 214 of the reamer 212. The reamer 212 follows the short guide wire 90 into the bone 14, drilling an opening as it moves inward into the bone 14. The reamer 212 also forms a declined slot in the end of the bone 14. The reamer 212, in a preferred embodiment penetrates into a bone 14, such as the tibia, up to 100 mm. The short guide wire 90 preferably extends beyond the end of the reamer 212. After the creation of the entry opening 210, the short guide wire 90 is removed and a box osteotome 216 is used to remove a larger piece of bone 14 that is in the shape of the head 30. The osteotome 216 is used to enlarge the entrance or opening 210 in the bone 14 by first horizontally inserting the box osteotome 216 then angling same to move away from the end 20 of the bone 14, thereby enlarging the opening toward the side surface 208 (see FIG. 19). The removal of a piece of the bone 14 allows the head 30 to be moved posteriorly upon insertion. The bone piece that is removed can be used later for a bone graft as needed.

Figures 20, 21:
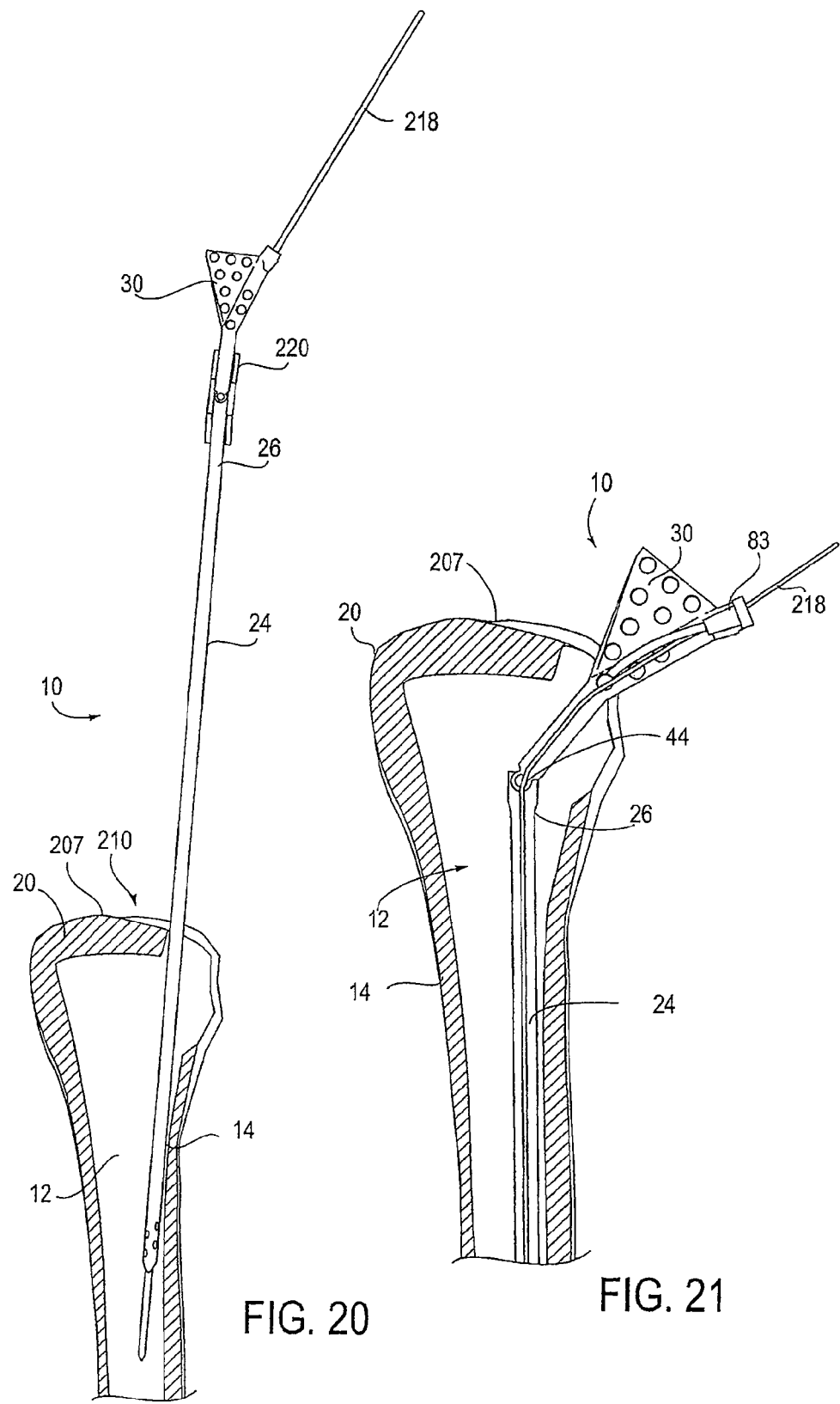
FIG. 20 is a cut away elevational view showing the insertion of the bone repair device of FIG. 1 into the bone.
FIG. 21 is a cutaway elevational view showing the continued insertion of the bone repair device pivoted as illustrated in FIG. 2 into the bone.

A long guide wire 218 may then be inserted into the bone 14 as illustrated in FIG. 20. The guide wire 90 is introduced into the interior of the bone 14 through the entry portal 210, the bone 14 being aligned to permit placement of the guide wire. The guide wire 218 is inserted into the bone 14 so as to extend from the first end 18 of the bone to a second end 20 of the bone 14. The guide wire 218 is threaded through the longitudinal passageways 88, 89 or channels in the intramedullary bone repair device 10, and is used to assist in insertion of the bone repair device 10 into the bone 14.

Figure 22:
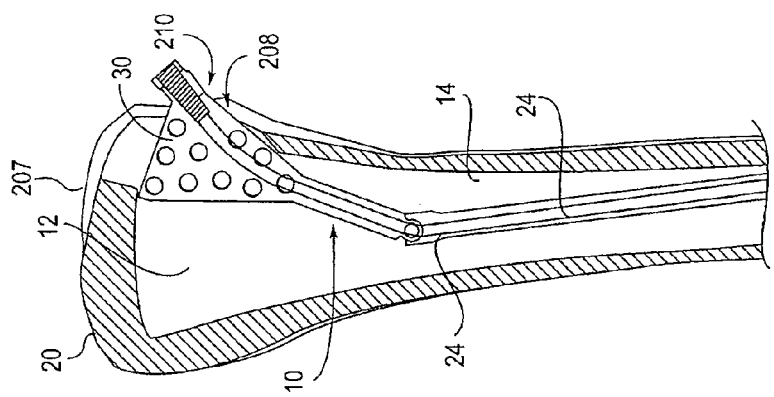
FIG. 22 is a cutaway elevational view showing the continued insertion of the bone repair device of FIG. 2 into the bone prior to attachment of the insertion tool.

Once the opening 210 is created and the long guide wire 218 is inserted, the bone repair device 10 is threaded over the guide wire 218 and inserted into the area or canal 12 in the interior of the bone 14 (see FIG. 22). This method comprises inserting an elongate body 10 having an enlarged head 30 and an elongate shaft 24 extending distally of the head 30 completely into the bone 14 so that the enlarged head 30 is in the vicinity of the joint. Specifically, the intramedullary bone repair device 10 is introduced into the interior 12 of the bone 14 by extending it over the guide wire 218 exposed within the bone 14. The intramedullary bone repair device 10 is inserted into the bone 14 at end 18 of the bone 14, through the insertion opening 210, and over the guide wire 90. To insert the intramedullary bone repair device 10 into the bone 14, the shaft 24 of the bone repair device 10 is initially impacted into the bone 14. To keep the head 30 positioned in line above the shaft 24 as the bone repair device 10 is inserted into the bone at the early stages of insertion, a clip 220, such as the C-shape clip, is used. Alternatively, the locking assembly 34 may be used to secure the head 30 above the shaft 24.

The head 30 is pivotable relative to the shaft 24 to facilitate insertion into the insertion opening in the bone 14. Shortly before the locking assembly 34 of the bone repair device 10 is inserted into the bone 14, the C-clip 220, or screw 162 and nut 160 assembly of the locking device, is removed. The removal of the restrictive device allows the head 30 to pivot relative to the shaft 24. Thus, before the device 10 is pushed further into the bone 14, the clip 220 is removed and the head 30 is declined. The declined or angled head 30 permits the continued insertion of the shaft 24 into the bone 14, yet allows utilization of an opening 210 that is not centered at the end 18 of the bone 14. For instance, a bone, such as a tibia, often has a second bone and/or other muscle structure, such as the knee-joint, positioned directly above the bone. In order to facilitate the insertion of the bone repair device 10 into the centerline of the bone 14, the device 10 must be inserted from a side surface 208 of the bone 14 and subsequently positioned along the centerline 38 of the bone 14.

The bone repair device 10 is further impacted into the bone 14. Insertion of the bone repair device continues until the bone repair device 10 is substantially received within the opening 210 of the bone 14 (see FIG. 22). As a result, the distal end 28 of the bone repair device 10 is positioned near the first end 18 of the bone 14 (see FIG. 22). The long guide wire 218 is then removed by pulling the wire out of the bone repair device 10. After removing the guide wire, the device 10 is pushed or impacted so that the head 30 is posteriorly pushed into the bone 14 into the opening 210 that has been formed by removal of the bone segment with the box osteotome 216.

In a preferred embodiment, as illustrated in FIG. 23, insertion jig 84, including anvil 206, yolk 202 and arm 204, is connected to the bone repair device 10 at the insertion tool attachment bore 78 or cylindrical collar 83 on the head 30 to facilitate further placement of the device 10 into the bone 14. Specifically, the external thread of the yolk 202 is threaded into the internal thread of the cylindrical collar 83, securing the jig to device 10. The jig 84, by applying pressure to the anvil 206, is used to push the head 30 toward the posterior, so as to pivot the head 30 into position in the bone 14, as shown in FIGS. 24-27 where the anvil 206 has been removed for purposes of simplicity. Once device 10 is in position, the targeting device or arm 204 is used to insert the screws 16 into the proximate bone 14 percutaneously. For example, openings 228 or pilot holes in arm 204 permit a sleeve and trocar assembly (not shown) to be carried by the targeting device. The trocar may be used to make an incision into tissue where necessary. The trocar is removed and the drill or drill bit 230 is placed through the inner sleeve 226 or opening 228 for drilling a hole in the bone 14 for attachment of a screw 16. The drill is then removed. The inner sleeve 226 is also removed from the outer sleeve which remains attached to the targeting device. The outer sleeve 232 is utilized for placement of the screw in the bone 14 and attachment to the head 30.

The head 30, at this point, is also positioned so as to be centered above the shaft 24 and along the centerline of the bone 14. The pivotal attachment permits the head 30, after the shaft 24 has been pushed into the bone 14, to be pivoted toward the centerline of the bone 14 and shaft 24. After the head 30 is positioned so as to be centered above the shaft 24, the locking assembly 34 is locked into place. An opening is formed in the bone 14 corresponding to the position of the pivot members 100, 106 of the intramedullary bone repair device 10. The nut 160, which serves as a "key" is inserted into the opening in the bone 14 and into the aligned openings 132, 138 in the pivot members so as to lock the locking assembly 34. The nut 160 may be inserted using an insertion sleeve 232 attached to the arm 204 of the jig 84. A hex key or other tool is also provided for the rotatable insertion of the screw 162 into the nut 160 or sleeve which locks the locking assembly 34 pivot members in place. Subsequently, screws 16 are inserted into position, attaching the plurality of bone segments of the fractured bone 14 to the head 30 of the elongate body. Specifically, the bone 14 is affixed to the intramedullary bone repair device 10 by attaching a plurality of threaded members or screws 16 through openings in the bone 14 and into a plurality of threaded openings 36 provided in the intramedullary bone repair device 10. More specifically, using a drill 230, pilot hole openings are created in the bone 14 based upon the pilot holes in the arm 204 or plate of the jig 84. The plurality of openings in the bone 14 are drilled to correspond to the plurality of threaded bores 36 in the intramedullary bone repair device 10.

Threaded screws 16 are inserted into the openings in the bone 14. The threaded screws are threaded into the respective threaded bores 36 of the intramedullary bone repair device 10, by rotational insertion into position, locking the device 10 in position in the bone. The screws 16 may be inserted using the rotation of a hex key or other tool 232. (see FIG. 1). More specifically, a threaded screw is rotationally inserted through the bone 14, beginning at the point of the distal end 124 of the screw. The screw's external thread 60 engages the internal thread 52 of the bore 36 in the head 30. The screw continues rotation until the tapered central segment 125 of the screw seats against the tapered inner diameter 54 of the bore 36. Such seating of the screw 16 within the bore 36 of the head 30 limits the travel of the screw so as to desirably position the screw relative to the bone and the head 30 and enhances the engagement of the screw in the head. The proximal segment 122 of the screw remains on the insertion side of the bone repair device 10. The distal segment 124 of the screw extends beyond the bone repair device 10 on the exit side. In this position, the distal segment or end 124 of the screw 16 is threaded into bone 14 opposite the insertion point, while the proximal segment or end 122 is also in contact with the bone 14 on the insertion side. Once the screws 16 are secured in position, the insertion tool 84 is removed and the incision is closed.

A plurality of screws 16 may also be inserted at the distal end 28 of the shaft 24. Specifically, after inserting the screws 16 into the head 30 of the device 10, the shaft 24 may be locked into the bone 14 at the distal end 28 of the shaft. Screws 16 are inserted percutaneously using a known free-hand technique, such as, but not limited to, fluoroscopy, which does not typically use a targeting device. In a preferred embodiment, screws are inserted into the plurality of bores 37 near the distal end 28 of shaft 24. The incision is subsequently closed.

In a preferred embodiment, the bone repair device 10 inserted into the bone 14 using the foregoing method supports a significant load as the bone heals. Ultimately, in a desired outcome, once the bone 14 properly heals it assumes almost all of the actual load of the patient. In this situation, the device 10 would assume only a fraction of the load and be relatively inactive.

Although various representative embodiments of this invention have been described above with a certain degree of particularity, those skilled in the art could make numerous alterations to the disclosed embodiments without departing from the spirit or scope of the inventive subject matter set forth in the specification and claims. For example, similar devices for treating distal tibia fractures, humerus fractures and femur fractures can be provided and can include design modifications to allow for anatomic variations and entry site restrictions with respect to such applications. Such changes could include variations in sizes to accommodate the treated bone, angles to facilitate entry of the device into the bone and the extent or degree of pivoting of the head relative to the shaft of the device.

It is appreciated that variations in the structure of the device can be provided and be within the scope of the present invention. For example, a device can be provided in which the neck 68 and shaft 24 are formed integral with each other, such as from a single piece of a shape memory alloy or other highly flexible or reconfigurable material, so as to allow for flexibility of the device during insertion and rigidity in the device after placement. Such rigidity could be provided by a change in temperature of the device due to warming by the body or by an application of an electrical charge to the device after insertion or other changes in characteristics of the device. Pivot assembly 44 and locking assembly 34 could be eliminated, as not being necessary, in such a device. Alternatively, the neck 68 and shaft 24 can be formed integral with each other of an expandable material that has a relatively small diameter, so as to be bendable upon insertion, and is radially expandable, for example through inflation, after insertion so as to be relatively rigid after placement in the bone. In a further example, the pivot assembly 44 and locking assembly 34 can be replaced with a suitable linkage assembly such as currently found in certain flexible locking humeral nails.

Changes in the head 30 can also be provided, so for example to eliminate the need for pivot assembly 44 and locking assembly 34. In a first alternative embodiment (not shown), the head can be formed with a tubular or cylindrical portion, for example shaped like rib 47, having a longitudinal slot extending therethrough for pivotably receiving a fin or plate, for example shaped like the portion of head 30 formed from surfaces 66 and 67, having a plurality of threaded bores 36 therein for receiving a plurality of bone screws. The fin can be moveable from a first position, in which the fin is centered relative to the cylindrical portion, to a second position, in which the fin is off center the cylindrical portion and thus together with the cylindrical portion has a configuration similar to head 30. The fin can be inserted into the bone in the first position, in which the fin and cylindrical portion together have a relatively small side elevational profile, and then deployed into the second position and preferably locked in the second position, in which the fin and cylindrical portion together have a relatively large side elevational profile. In a second alternative embodiment (not shown), the head can be formed with a cylindrical portion, for example shaped like rib 47, having a longitudinal slot extending therethrough for receiving one or more plate-like elements, which when inserted adjacent each other into the slot of the cylindrical portion after insertion of the cylindrical portion into the bone have together with the cylindrical portion a configuration similar to head 30. The plate-like elements are provided with a plurality of threaded bores 36 therein. The insertion of the cylindrical portion, without the plate-like elements therein, reduces the transverse dimension of the head during insertion and thus can reduce the bending requirements of the device during insertion so as to eliminate the need for pivot assembly 44. In a third alternative embodiment, the head can be formed with a cylindrical portion, for example shaped like rib 47, having a longitudinal slot extending therethrough for receiving a plurality of planar fan segments which, after insertion of the cylindrical portion into the bone deploy in a fan-like manner from one or both sides of the cylindrical portion. The fan segments are provided with a plurality of threaded bores 36 therein. The deployed fan segments can have, together with the cylindrical portion, a configuration similar to head 30.

All directional references (e.g., upper, lower, upward, downward, left, right, leftward, rightward, top, bottom, above, below, vertical, horizontal, clockwise, counterclockwise, x-axis, y-axis, and z-axis) are only used for identification purposes to aid the reader's understanding of the embodiments of the present invention, and do not create limitations, particularly as to the position, orientation, or use of the invention unless specifically set forth in the claims. Joinder references (e.g., attached, coupled, connected) are to be construed broadly and may include intermediate members between a connection of elements and relative movement between elements. As such, joinder references do not necessarily infer that two elements are directly connected and in fixed relation to each other.

In some instances, components are descried with reference to "ends" having a particular characteristic and/or being connected with another part. However, those skilled in the art will recognize that the present invention is not limited to components which terminate immediately beyond their points of connection with other parts. Thus, the term "end" should be interpreted broadly, in a manner that includes areas adjacent, rearward, forward of, or otherwise near the terminus of a particular element, link, component, part, member. In methodologies directly or indirectly set forth herein, various steps and operations are described in one possible order of operation, but those skilled in the art will recognize that steps and operations may be rearranged, replaced, or eliminated without necessarily departing from the spirit and scope of the present invention. It is intended that all matter contained in the above description or shown in the accompanying drawings shall be interpreted as illustrative only and not limiting. Changes in detail or structure may be made without departing from the spirit of the invention as defined in the appended claims.

Although the present invention has been described with reference to preferred embodiments, persons skilled in the art will recognize that changes may be made in form and detail without departing from the spirit and scope of the invention.

What is claimed is:

1. An intramedullary bone repair device for insertion into a bone extending along a centerline and for use with a plurality of screws comprising an elongate shaft having a longitudinal axis and a proximal end and a distal end, a head coupled to the proximal end of the shaft for pivoting about an axis inclined relative to the longitudinal axis of the shaft, the distal end of the shaft having a tapered end for facilitating insertion of the shaft along the centerline of the bone, and a locking assembly carried by the proximal end of the shaft and the head for rigidly coupling the shaft and the head together when the shaft and head have been desirably positioned within the bone, the head being substantially triangular in shape and the shaft and the head being provided with a plurality of threaded bores for receiving the plurality of screws to affix the shaft and head within the bone.

2. The device of claim 1 wherein the head is coupled to the proximal end of the shaft for pivoting about an axis extending substantially perpendicular to the longitudinal axis of the shaft.

3. The device of claim 2 wherein the plurality of threaded bores in the head extend parallel to each other.

4. The device of claim 1, wherein the proximal end of the shaft has a first pivot member and the head has a second pivot member for mating with the first pivot member.

5. The device of claim 1, wherein the shaft is provided with a first longitudinal passageway and the head is provided with a second longitudinal passageway for receiving a guide wire.

6. The device of claim 1, wherein the locking assembly includes a stopper positioned on the proximal end of the shaft.

7. The device of claim 1, wherein the head has an external surface and an internal thread extending inwardly from the external surface for forming an internal bore, the internal thread having an inner diameter that tapers inwardly from the external surface whereby an externally-threaded screw having a tapered threaded portion can be seated in the internal bore of the head when affixing the head to the bone.

8. The device of claim 7, wherein the internal thread has an outer diameter that is constant and the inner diameter tapers to a minimum inner diameter whereby an externally threaded screw provided with an external thread having an outer diameter approximating the outer diameter of the internal thread and an inner diameter approximating the minimum inner diameter of the internal thread can be seated in the internal bore of the head when affixing the head to the bone.

9. The device of claim 1 wherein the tapered distal end of the shaft is rounded.

10. An intramedullary bone repair device for insertion into a bone extending along a centerline comprising a shaft having a proximal end and a distal end, the distal end of the shaft having a tapered end for facilitating insertion of the shaft along the centerline of the bone, and a head attached to the proximal end of the shaft by means of a pivotal connection that includes means carried by the proximal end of the shaft and the head for rigidly coupling together the shaft and the head when the shaft and head have been properly positioned within the bone, the head having first and second surfaces that taper inwardly towards the shaft so as to be substantially triangular in plan and being provided with a plurality of threaded bores for receiving a plurality of screws to affix the plate-like head to the bone.

11. The device of claim 10, wherein the shaft and the head extend substantially within a plane so as to be positionable within the bone and along the centerline of the bone.

12. An intramedullary bone repair device comprising a shaft having a proximal end and a distal end, the distal end of the shaft having a tapered end for facilitating insertion of the shaft along the center of the bone, and a head attached to the proximal end of the shaft, the head tapering inwardly toward the shaft and including a substantially cylindrical side portion and a plate extending outwardly from the side portion, the plate being provided with a plurality of threaded bores for receiving a plurality of screws to affix the plate-like head to the bone.

13. The device of claim 12 wherein the head is substantially triangular in plan.

* * * * *